United States Patent [19]

Burkhardt et al.

[11] 4,310,626

[45] Jan. 12, 1982

[54] INTERFERENCE-RESISTANT COMPOSITION, DEVICE AND METHOD FOR DETERMINING A PEROXIDATIVELY ACTIVE SUBSTANCE IN A TEST SAMPLE

[75] Inventors: Alan E. Burkhardt, Elkhart, Ind.; Ann M. Tideman, Edwardsburg, Mich.

[73] Assignee: Miles Laboratories, Inc., Elkhart, Ind.

[21] Appl. No.: 155,318

[22] Filed: Jun. 2, 1980

[51] Int. Cl.$^3$ .............................................. C12Q 1/28
[52] U.S. Cl. ..................................... 435/28; 435/188; 435/805; 23/230 B; 23/931; 252/408
[58] Field of Search ................... 435/28, 14, 188, 805; 23/230 B, 931; 252/408 R

[56] References Cited

U.S. PATENT DOCUMENTS

| T978,003 | 1/1979 | Wu et al. | 435/28 |
|---|---|---|---|
| 3,411,887 | 11/1968 | Ku | 23/230 B |
| 3,770,381 | 11/1973 | Schmitt | 435/28 |
| 4,017,261 | 4/1977 | Svoboda et al. | 435/28 |
| 4,168,205 | 9/1979 | Danninger et al. | 435/28 |
| 4,228,240 | 10/1980 | Dawson et al. | 435/188 |

OTHER PUBLICATIONS

Iwasaki T., *Journal of the Chemical Society of Japan*, 63, pp. 820-826 (1942).
I. M. Reibel, "Decomposition of Hydrogen Peroxide Solutions in the Presence of Trivalent Cobalt Complex Compounds", Khim. Perekismykh Soedin. Akad. Nauk SSS Inst. Okis. i Neorgan Khim., (1963) pp. 68-79.
"The Merck Index", Ninth Edition, Merck & Co. Inc., Rahway, (1976), p. 311.

*Primary Examiner*—Benoît Castel
*Attorney, Agent, or Firm*—Edward H. Gorman, Jr.

[57] ABSTRACT

A composition, test device and method of use in determining the presence of a peroxidatively active component in a test sample are disclosed. The composition comprises an organic peroxide, an indicator capable of providing a detectable response in the presence of the peroxide and a peroxidatively active substance, and a complex of Co(III). Inclusion of the Co(III) complex renders the composition resistant to the adverse effects of ascorbate, which might be present in the test sample. The test device comprises a carrier matrix incorporated with the composition. The method comprises contacting the test sample with the device and observing a detectable response therein.

23 Claims, No Drawings

INTERFERENCE-RESISTANT COMPOSITION, DEVICE AND METHOD FOR DETERMINING A PEROXIDATIVELY ACTIVE SUBSTANCE IN A TEST SAMPLE

BACKGROUND OF THE INVENTION

1. Field of the Invention

The present invention relates to the determination of a peroxidatively active substance in a test sample. More particularly, the invention relates to a composition for such determination which is resistant to possible adverse effects from ascorbic acid which might also be present in the sample.

Many analytical methods are presently available for detecting the presence of peroxidatively active substances in samples such as urine, fecal suspensions, and gastrointestinal contents. Hemoglobin and its derivatives are typical of such "peroxidatively active" substances because they behave in a manner similar to the enzyme peroxidase. Such substances have also been referred to as pseudoperoxidases. Peroxidatively active substances are enzyme-like in that they catalyze the redox reaction between peroxides and such indicator compounds as benzidine, o-tolidine, 3,3',5,5'-tetramethylbenzidine, 2,7-diaminofluorene or similar indicator substances, thereby producing a detectable response such as a color change. Hence, most methods for determining the presence of occult blood in test samples rely on this pseudoperoxidase activity.

2. Description of the Prior Art

Several methods have evolved over the years which rely on enzyme-like catalysis of the peroxidic oxidation of color-forming indicators. Primarily these include wet chemical procedures and "dip-and-read" type reagent-bearing strips. Of the former, a typical example is set forth in Richard M. Henry, et al., *Chemical Chemistry Principles and Techniques* (Hagerstown, Md.: Harper and Row, 1974), pp. 1124–1125. This procedure involves the use of glacial acetic acid (buffer), diphenylamine (indicator), and hydrogen peroxide. While such wet methods have proven analytical ability, they are nevertheless fraught with obvious shortcomings, not the least of which are poor reagent stability and inadequate sensitivity.

A second method for the determination of peroxidatively active substances, and the one presently preferred by most clinical assayists and analysts, utilizes the so-called "dip-and-read" reagent strips. Typical of such devices are reagent strips manufactured by the Ames Division of Miles Laboratories, Inc. and sold under the name HEMASTIX ®. These comprise, in essence, a porous paper matrix affixed to a plastic strip or handle. The matrix is impregnated with a buffered mixture of an organic hydroperoxide and o-tolidine. Upon immersion in a liquid containing hemoglobin, myoglobin, erythrocytes or other pseudoperoxidases, a blue color develops in the matrix, the intensity of which is proportional to the concentration of the peroxidatively active substance in the sample. Thus, by comparing the color developed in the matrix to a standard color chart, the assayist can determine, on a semiquantitative basis, the amount of analyte present in the sample.

The advantages of reagent strips over wet chemistry methods are predominantly twofold; strips are easier to use because neither the preparation of reagents nor the attendant apparatus is required; and greater stability of reagents is afforded, resulting in improved accuracy, sensitivity and economy.

But whether the analysis for the peroxidatively active species be through either alternative, a problem inherent to both exists for which there has to date been no satisfactory solution: interference due to the presence of ascorbate or other reducing agent in the test sample. In the case or urinalysis, for example, the recent popularity of diets which include high dosages of vitamin C (ascorbic acid) has led to serious problems in analyzing for such urine constituents as occult blood, since patients on such diets invariably have atypically elevated levels of urinary ascorbate.

The adverse effects of reducing agents such as ascorbate were recognized as early as 1938. R. Kohn and R. M. Watrous, *Journal of Biological Chemistry*, 124, 163–168 (1938). That the same problem still plagues this area of analysis is evidenced by a proposal in 1979 that when an occult blood (pseudoperoxidase) analysis in urine is performed, a simultaneous ascorbate analysis be performed in order to gauge the accuracy of the occult blood determination. L. Nielsen, P. J. Jorgensen and A. C. Hansen, *Ugeskrift for Laeger*, 141, 791–793 (1979).

Although many attempts at removing ascorbate interference with other test systems, such as glucose-sensitive reagents, are reported in the literature, to data no successful attempts have been reported whereby the determination of peroxidatively active substances has been rendered immune to these adverse effects. With the glucose-sensitive systems, approaches range from filtering out ascorbate before it reaches the reagents to utilizing an enzyme to decompose it in situ.

Thus, Canadian Pat. No 844,564, issued on June 16, 1970, to Dahlqvist discloses a device for glucose determination in urine or other media which includes, in addition to a porous portion impregnated with normal glucose-responsive reagents, an additional portion to receive the urine test sample. The sample-receiving portion comprises an ion exchange material, whose singular function in the device is to adsorb any ascorbate which might be present in the urine sample.

Another approach to alleviating ascorbate interference is reflected in U.S. Pat. No. 4,168,205, which issued on Sept. 18, 1979, To Danninger et al. This reference suggests incorporating the enzyme ascorbate oxidase into the test reagent formulation, the theory being that if ascorbate is present in the sample it will be enzymatically oxidized to dehydroascorbate, a compound which does not adversely effect the desired analysis.

U.S. Pat. No. 3,411,887, which issued to Ku on Nov. 19, 1968, describes a way of eliminating ascorbate interference with reagent systems which rely on enzymatic oxidizing substances such as glucose oxidase. An ascorbate "trapping system" is employed. This comprises an "ionizable heavy metal compound which, when in an ionized state possesses an oxidation-reduction potential $E_{red}°$ between that of the redox indicator dye . . . and that of [ascorbate]". Many metals are cited as examples, including cobalt, iron, mercury and nickel.

In addition to these studies, attention to the ascorbate problem with glucose tests is manifested by:

1. H. Gifford, et al., *J. Amer. Med. Assoc.*, 178, 149–150 (1961).
2. P. O'Gorman, et al., *Brit, Med. J.*, 603–606 (1960).
3. R. Brandt, et al., *Clin. Chem, Acta*, 51, 103–104 (1974).
4. R. Brandt, et al., *Am. J. Clin. Pathol.*, 68, 592–594 (1977).

Like the above-cited Ku patent other references deal with the complexing and oxidation of ascorbate using cobalt. G. Bragagnolo (*Ann. Chim. Applicata,* 31, 350-368, 1941) reported that solutions of ascorbic acid were oxidized by air in the presence of cobalt metal. Similar activity has been reported for Co(NH$_3$)$_6$Cl$_3$ by Tomokichi Iwasaki in *Journal of the Chemical Society of Japan,* 63, 820-826 (1942).

Significantly, although the prior art deals extensively with glucose analysis, it appears bereft of suggestions as to how to solve the ascorbate interference problem with the determination of peroxidatively active substances such as peroxidase and occult blood (hemoglobin). The disclosure in U.S. Pat. No. 3,411,887 (see above) notwithstanding, the prior art unequivocally teaches that metal ions, such as Co(III), are in fact pseudoperoxidases. For example, Co(III) acetate is used commercially to catalytically decompose cumene hydroperoxide. *The Merck Index,* 9th Ed., Page 311 (1976). A series of Co(III) complexes are reported to catalytically decompose peroxides by Kh. Lohs., *Monatsber, Deut. Akad. Wiss, Berlin,* 8, 657-659 (1966) (See *Chemical Abstracts,* 67, 120383z. 1967).

As is stated supra, the present invention deals with improving the present state-of-the-art system for determining peroxidatively active substances. Such systems invariably comprise an organic hydroperoxide and a redox indicator such as o-tolidine or 3,3',5,5'-tetramethyl benzidine. The analyte, because it mimics the enzyme peroxidase, causes a reaction between the indicator and organic hydroperoxide which yields a color, the intensity of which is a barometer of the analyte concentration. In light of the unmistakable teachings of peroxidase activity shown by Co(III) complexes, one skilled in the art would clearly not expect such a substance to be compatible with the peroxide/indicator system. Clearly, if one incorporates an analyte into the very reagent formulation designed to change color in the presence of that analyte, it is to be expected that false positive results would be obtained. These conclusions notwithstanding, it has been surprisingly found that the peroxidatively active Co(III) complexes not only fail to give false positive results, but they actually improve the reagent system, making it even more dependable, i.e., less sensitive to the inaccuracies caused by ascorbate interference.

SUMMARY OF THE INVENTION

Briefly stated, the present invention relates to a composition for detecting the presence of a peroxidatively active substance in a test sample, and to a device incorporating the composition, wherein the device is resistant to the interfering effects of ascorbic acid present in the sample. A method for using the device is likewise within the ambit of invention disclosed herein, as is the process for making it. The composition comprises an organic hydroperoxide and an indicator capable of providing a detectable response such as a color change, in the presence of the peroxidatively active substance and peroxide. It additionally comprises a complex of Co(III). It is this latter component which appears responsible for providing the unexpected ascorbate resistance.

DETAILED DESCRIPTION OF THE INVENTION

The organic hydroperoxide contemplated for use in the test composition can be selected from many well-known organic hydroperoxides. It must, however, be capable of interacting with a peroxidatively active substance in the presence of an indicator to produce a detectable response such as a color change or change in the amount of light absorbed or reflected by the test composition. Among hydroperoxides which have been found suitable are t-butyl hydroperoxide, cumene hydroperoxide, diisopropylbenzene hydroperoxide, 2,5-dimethylhexane-2,5-dihydroperoxide, paramenthane hydroperoxide or mixtures thereof. Of these, cumene hydroperoxide has been found to be most preferable.

There exist many indicators which are capable of producing a detectable response in the presence of an organic hydroperoxide and a peroxidatively active substance and which are, therefore, suitable for use in the present invention. For the most part, these include the so-called "benzidine-type" compounds. Typical of these are benzidine, o-tolidine, 3,3', 5,5'-tetra (lower alkyl) benzidine, 2,7-diaminofluorene or mixtures of these in varying proportions. By "lower alkyl" is meant an alkyl radical having 1 to 6 carbon atoms, including methyl, ethyl, n-propyl and isopropyl, and the various butyl, pentyl and hexyl isomers.

The Co(III) complexes useful in the present invention include Co(NH$_3$)$_6$Cl$_3$, [Co(NH$_3$)$_5$H$_2$O]Cl$_3$, and [Co(NH$_3$)$_5$CO$_3$]NO$_3$. Of course, it is understood that many other cobalt (III) complexes are adaptable to the invention given the teachings herein. It has been found that Co(NH$_3$)$_6$Cl$_3$ provides excellent results, and is the preferred complex for achieving abatement of ascorbate interference. In a preferred embodiment of the present invention, the composition comprises cumene hydroperoxide, 3,3',5,5'-tetramethylbenzidine and Co(NH$_3$)$_6$Cl$_3$.

Preparation of the test device includes incorporating the composition with a suitable carrier matrix, and the latter can take on a multitude of forms. Thus, U.S. Pat. No. 3,846,247 teaches the use of felt, porous ceramic strips, and woven or matted glass fibers. Additionally, U.S. Pat. No. 3,552,928 teaches the use of wood sticks, cloth, sponge material, and argillaceous substances. The use of synthetic resin fleeces and glass fiber felts as a carrier matrix is suggested in British Pat. No. 1,369,139. Another British Pat. No. 1,349,623, proposes the use of light-permeable meshwork of thin filaments as a cover for an underlying paper matrix. Polyamide fibers are taught in French Pat. No. 2,170,397. These suggestions notwithstanding, however, the material predominantly used in the art as a carrier matrix, and that which is especially suitable for the present invention, is a bibulous paper such as filter paper. It can thus be seen that there is a great deal of leeway in selecting an appropriate material for use as a carrier matrix, and the matrix can take on various physical forms. All of these types are intended as being within the scope of the present invention.

The composition of the present invention can be incorporated with the carrier matrix in a variety of ways. The ingredients can be dissolved or suspended in water or other suitable solvent, such as chloroform, methylene chloride, methanol, cyclohexane and mixtures thereof. Such a solution or suspension can then be used to impregnate filter paper, as an ink wherein the reagents are printed on a suitable matrix, or the carrier matrix can be coated with the composition, such as with a doctor blade.

The presently preferred method is to impregnate filter paper with a solution or suspension of the composition, the preferred solvent being distilled or deionized water. Impregnation can be accomplished by dipping a piece of filter paper into the solution and drying the dipped paper in an air oven. The dried paper is then cut into a square measuring about 0.5 cm on a side, which is then mounted on one end of a polystyrene film strip measuring about 0.6×10 cm. Mounting is accomplished through use of double faced adhesive tape, such as that available from the 3M Co., known as Double Stick.

Especially preferred in formulating the device of the present invention is the method wherein the Co(III) complex is introduced into the filter paper as an aqueous first dip. Thus, the filter paper is first impregnated with the cobalt complex solution, dried, reimpregnated with an aqueous second dip of the organic hydroperoxide and indicator, and dried a second time. Such a two-dip process, where the cobalt complex is impregnated into the paper before the other reagents, has been found to yield a test device having far greater ascorbate resistance than strips prepared in a process whereby the cobalt complex is applied as a second dip.

The following examples are provided to further illustrate the concepts and advantages of the presently disclosed invention. They show how to make and use the invention, and present comparative data demonstrating the improved ascorbate resistance it provides. These examples are, however, not to be interpreted as limiting in any way the scope of the invention.

A. THE TEST COMPOSITION

Example I—$Co(NH_3)Cl_6$

An experiment was conducted wherein the composition of the present invention, capable of determining the presence of peroxidase or a peroxidatively active substance in a test sample, was prepared. Thus, the following ingredients were combined in the order listed.

| Distilled water | 50 ml.* |
|---|---|
| Sodium citrate | 2.13 g** |
| Citric acid | 2.77 g |
| Triethanolamine borate | 5.00 g |
| Methyl sulfone | 6.67 g |
| Sodium lauryl sulfate | 0.75 g |
| Ethylenediaminetetracetic acid | 0.13 g |
| Dimethylformamide | 50.0 ml |
| 5-Methoxyquinoline | 0.4 ml |
| Cumene hydroperoxide | 2.0 ml |
| 3,3',5,5'-Tetramethylbenzidine | 0.60 g |
| $Co(NH_3)_6Cl_3$ | 0.15 g |

*milliliters
**grams

This composition is found to yield a blue color when contacted with an aliquot of a urine sample containing 0.135 milligram of hemoglobin per deciliter.

Example II—Cobalt (III) Acetylacetonate

The experiment of Example I was repeated except that cobalt (III) acetylacetonate was used (0.20 g/100 ml) in place of $Co(NH_3)_6Cl_3$. This composition forms a blue color when contacted with a urine sample aliquot containing 0.135 milligram of hemoglobin per deciliter.

Example III—$[Co(NH_3)_5H_2O]Cl_3$

The experiment of Example I was repeated except that $[Co(NH_3)_6H_2O]Cl_3$ was used (0.15 g/100 ml) in place of $Co(NH_3)_6Cl_3$. This composition forms a blue color when contacted with a urine sample aliquot containing 0.135 milligram of hemoglobin per deciliter.

Example IV—$[Co(NH_3)_5CO_3]NO_3$

The experiment of Example I was repeated except that $[Co(NH_3)_5CO_3]NO_3$ was used (0.15 g/100 ml) in place of $Co(NH_3)_6Cl_3$. This composition forms a blue color when contacted with a urine sample aliquot containing 0.135 milligram of hemoglobin per deciliter.

Example V—$[Co(NH_3)_4CO_3]NO_3.3H_2O$

The experiment of Example I was repeated except that $[CO(NH_3)_4CO_3]NO_3.3H_2O$ was used (0.17 g/100 ml) in place of $Co(NH_3)_6Cl_3$. This composition forms a blue color when contacted with a urine sample aliquot containing 0.135 milligrams of hemoglobin per deciliter.

B. THE TEST DEVICE cl Example

VI—$Co(NH_3)_6Cl_3$

An experiment was conducted whereby a test device was prepared comprising a paper carrier matrix incorporated with the composition of Example I.

Laboratory filter paper (Eaton & Dikeman No. 237) was impregnated with $Co(NH_3)_6Cl_3$ and the remaining ingredients of Example I in a two-dip process. Accordingly, a first dip was prepared by dissolving $Co(NH_3)_6Cl_3$ in distilled water to a concentration of 0.15 gram per 100 milliliters. The paper was dipped in this solution and dried for 12 minutes in an air oven at 95° C.

A second dip was prepared by mixing the following ingredients in the order as listed:

| Distilled water | 50 ml.* |
|---|---|
| Sodium citrate | 2.13 g** |
| Citric acid | 2.77 g |
| Triethanolamine borate | 5.00 g |
| Methyl sulfone | 6.67 g |
| Sodium lauryl sulfate | 0.75 g |
| Ethylenediaminetetracetic acid | 0.13 g |
| Dimethylformamide | 50.0 ml |
| 6-Methoxyquinoline | 0.4 ml |
| Cumene hydroperoxide | 2.0 ml |
| 3, 3', 5, 5'-Tetramethylbenzidine | 0.60 g |

*milliliters
**grams

The dried paper containing the first dip residue was immersed in the second dip and dried at 95° C. for 12 minutes in an air oven.

Assembly of the test device comprised applying a 0.6 centimeter (cm.) square of the dried, impregnated paper to one end of a polystyrene film strip measuring 0.6 by 10 cm using double faced adhesive tape (3M Company, Double Stick 415).

Testing of the device in urine containing both hemoglobin and ascorbate yielded easily discernible color levels corresponding to various hemoglobin concentrations.

Example VII—Cobalt (III) acetylacetonate

The experiment of Example VI was repeated except that the paper carrier matrix was incorporated with the composition of Example II, i.e., a 0.20 gram per 100 milliliters solution of Cobalt (III) acetylacetonate was used in place of the $Co(NH_3)_6Cl_3$ solution. Testing of the device in urine containing both hemoglobin and ascorbate yielded easily discernible color levels corresponding to various hemoglobin levels.

Example VIII—[Co(NH$_3$)$_5$H$_2$O]Cl$_3$

The experiment of Example VI was repeated except that the paper carrier matrix was incorporated with the composition of Example III, i.e., a 0.15 gram per 100 milliliters solution of [Co(NH$_3$)$_5$H$_2$O]Cl$_3$ was used in place of the Co(NH$_3$)$_6$Cl$_3$ solution. Testing of the device in urine containing both hemoglobin and ascorbate yielded easily discernible color levels corresponding to various hemoglobin levels.

Example IX—[Co(NH$_3$)$_5$CO$_3$]NO$_3$

The experiment of Example VI was repeated except that the paper carrier matrix was incorporated with the composition of Example IV, i.e., a 0.15 gram per 100 milliliters solution of [Co(NH$_3$)$_4$CO$_3$]NO$_3$ was used in place of the Co(NH$_3$)$_6$Cl$_3$ solution. Testing of the device in urine containing both hemoglobin and ascorbate yielded easily discernible color levels corresponding to various hemoglobin levels.

Example X—[Co(NH$_3$)$_4$CO$_3$]NO$_3$.3H$_2$O

The experiment of Example VI was repeated except that the paper carrier matrix was incorporated with the composition of Example V, i.e., a 0.17 gram per 100 milliliters solution of [Co(NH$_3$)$_4$CO$_3$]NO$_3$.3H$_2$O was used in place of the Co(NH$_3$)$_3$Cl$_3$ solution. Testing of the device in urine containing both hemoglobin and ascorbate yielded easily discernible color levels corresponding to various hemoglobin levels.

C. ASCORBATE INTERFERENCE

Example Xi—Co(NH$_3$)$_6$Cl$_3$

A series of experiments was conducted in order to study the effects of ascorbate on the test devices of the present invention.

Test strips were prepared as described in Examine VI. In addition, control test strips were prepared in exactly the same manner except that the cobalt complex was omitted, i.e., only the second dip was used to impregnate the filter paper carrier matrix. These strips were tested by dipping into test samples comprising negative urine, and aliquots thereof to which had been added human whole blood, ascorbic acid or both.

The appearance of color was noted visually after one minute and assigned a numerical value corresponding to relative color intensity. Thus, a control strip was dipped into urine samples containing various concentrations of hemoglobin, but no ascorbate. Color values were assigned as follows

| Hemoglobin (mg/%) | 0 | 0.015 | 0.045 | 0.135 | 0.405 |
|---|---|---|---|---|---|
| Color value | 0 | 10 | 20 | 30 | 40 |

Thus the color formed in the control device upon being dipped in a urine sample having no hemoglobin present was ascribed a color value of 0; whereas the color produced by a urine containing 0.405 milligrams hemoglobin per 100 milliliters was assigned the value of 40.

The results are as follows:

| Urine Sample | | Visual Results after 1 Min. | |
|---|---|---|---|
| Hemoglobin (mg/%) | Ascorbic Acid (mg/%) | Control | Test Device |
| 0 | 0 | 0 | 0 |
| 0.045 | 0 | 25 | 25 |
| 0.045 | 50 | 2 | 8 |
| 0.135 | 0 | 30 | 32 |
| 0.135 | 50 | 13 | 22 |

As can be seen from the data, the test device containing the cobalt complex was markedly improved over the control device having no cobalt complex.

Example XII—Cobalt (III) Acetylacetonate

Experiments similar to those of Example XI were conducted with the devices prepared in Example VII.

Instead of using the visual observation technique of Example XI, color formation was followed using a device known as the "Rapid Scanner". This device is a scanning reflectance spectrophotometer interfaced with a PDP-12 computer obtained from the Digital Equipment Corporation. The instrument is used for the rapid measurement of reflectance spectra in the visual range. The computer allows for the storage of spectral data and computations. Measurements of the performances of reagent strips in the Rapid Scanner have the following advantages over visual observations of the same strips:

1. The light source and conditions surrounding the sample remain fixed. In visual readings the light source can vary, not only in wavelength components, but also in relation to the location of the strip being observed.

2. The detector characteristics remain fixed with the Rapid Scanner. In visual observation, the detector (i.e., the eyes of the observer) varies from person to person, and with the same person, from day to day.

3. The Rapid Scanner allows more precise quantitation of the data than does human observation, thereby permitting comparisons between results to be made in a more objective manner than with visual observation.

The Rapid Scanner instrument was constructed by the Ames Company Division of Miles Laboratories, Inc., Elkhart, Ind., U.S.A., from whom complete information with respect to structural and performance characteristics are obtainable.

Tri-stimulus values from the Rapid Scanner were used to calculate color difference values ($\Delta E$) according to the convention contained within "Supplement No. 2 to Commission Internationale de L'Eclairage (Paris, France) Publication No. 15, Colorimetry, (E.-1. 3.1), 1971." The data from this instrument are therefore recorded below in terms of $\Delta E$, or color difference units.

Thus, as in Example XI, control devices with no Co(III) complex were compared with those from Example VII which contained Co(III) acetylacetonate. The comparison was performed using urines containing various hemoglobin levels with and without ascorbate.

The color difference units ($\Delta E$) provided by the Rapid Scanner correspond to hemoglobin levels (in the absence of ascorbate) in accordance with the following:

| Hemoglobin (mg/%) | 0 | 0.015 | 0.030 | 0.045 | 0.135 |
|---|---|---|---|---|---|

| -continued | | | | | |
|---|---|---|---|---|---|
| ΔE | 0 | 40 | 50 | 58 | 63 |

This data was obtained from the Rapid Scanner using the control devices, i.e., devices prepared as in Example XII except that no Co(III) acetylacetonate was present.

When the devices containing the cobalt (III) acetylacetonate were tested in urine samples containing 0.135 mg% hemoglobin with and without ascorbate, the results were as follows:

| Urine Sample | | Rapid Scanner Results (ΔE) | |
|---|---|---|---|
| Hemo-globin (mg/%) | Ascorbic Acid (mg/%) | Control | Test Device |
| 0.135 | 0 | 63 | 57 |
| 0.135 | 50 | 18 | 35 |

The data shows significant abatement of ascorbate interference in the device containing the Co(III) complex, whereas the control exhibited serious ascorbate susceptibility.

Example XIII—[Co(NH₃)₅H₂O]Cl₃

The experiment of Example XII was repeated except that the devices of Example VIII were evaluated, i.e., devices containing [Co(NH₃)₅H₂O]Cl₃. The results are as follows:

| Urine Sample | | Rapid Scanner Results (ΔE) | |
|---|---|---|---|
| Hemo-globin (mg/%) | Ascorbic Acid (mg/%) | Control | Test Device |
| 0.135 | 0 | 63 | 60 |
| 0.135 | 50 | 18 | 27 |

The data reflects less ascorbate susceptibility due to the presence of the cobalt (III) complex.

Example XIV—[Co(NH₃)₅CO₃]NO₃

The experiment of Example XII was repeated except that the devices of Example IX were evaluated, i.e., devices containing [Co(NH₃)₅CO₃]NO₃. The results are as follows:

| Urine Sample | | Rapid Scanner Results | |
|---|---|---|---|
| Hemo-globin (mg/%) | Ascorbic Acid (mg/%) | Control | Test Device |
| 0.135 | 0 | 63 | 62 |
| 0.135 | 50 | 18 | 43 |

The data reflects a significant reduction in ascorbate susceptibility due to the presence of the cobalt (III) complex.

Example XV—[Co(NH₃)₄CO₃]NO₃·3H₂O

The experiment of Example XII was repeated except that the devices of Example X were evaluated, i.e., devices containing [Co(NH₃)₄CO₃]NO₃·3H₂O. The results are as follows:

| Urine Sample | | Rapid Scanner Results | |
|---|---|---|---|
| Hemo-globin (mg/%) | Ascorbic Acid (mg/%) | Control | Test Device |
| 0.135 | 0 | 63 | 54 |
| 0.135 | 50 | 18 | 49 |

The table portrays data evidencing a dramatic reduction in ascorbate susceptibility due to the presence of the cobalt (III) complex.

D. STABILITY TESTING

Example XVI

Because of the prior art teachings of the peroxidative activity of cobalt (III), devices prepared as in Example VI and the control device (prepared as in Example VI except without the cobalt complex) were tested for stability. This experiment showed virtually no difference in stability between the present invention and the control devices, despite the fact that one would expect the cumene hydroperoxide in the composition to decompose rapidly in the presence of Co(III).

Some of the devices of Example VI, both cobalt-containing and control, were stressed by being stored for two weeks in an air oven at 50° C. These stressed strips, as well as unstressed strips, were then dipped in negative urine and negative urine to which had been added various amounts of human whole blood. The appearance of color was evaluated as in Example VI, i.e., visually after one minute. The data is as follows:

| Hemoglobin (mg/%) | Control Visual Results after 1 Minute | |
|---|---|---|
| | Unstressed | 2 wks. 50° C. |
| 0.000 | 0 | 0 |
| 0.015 | 20 | 19 |
| 0.030 | 22 | 21 |
| 0.045 | 25 | 25 |
| 0.135 | 30 | 32 |
| 0.405 | 40 | 40 |

| Hemoglobin (mg/%) | Present Invention Visual Results after 1 Minute | |
|---|---|---|
| | Unstressed | 2 wks. 50° C. |
| 0.000 | 0 | 0 |
| 0.015 | 20 | 18 |
| 0.030 | 21 | 21 |
| 0.045 | 25 | 23 |
| 0.135 | 32 | 30 |
| 0.405 | 40 | 40 |

As can be seen from the above data, no incompatibility between the peroxide and Co(III), even after storage at 50° C. for two weeks, is evident. Moreover, the cobalt-containing test devices are equally as sensitive as the control devices without the presence of cobalt (III).

What is claimed is:

1. In a composition for detecting the presence of a peroxidatively active substance in a test sample, the composition comprising an organic hydroperoxide selected from the group consisting of t-butyl hydroperoxide, cumene hydroperoxide, diisopropylbenzene hydroperoxide, 2,5-dimethylhexane-2,5 dihydroperoxide, paramenthane hydroperoxide, or mixtures thereof, and an indicator capable of providing a detectable response in the presence of peroxide and the peroxidatively active substance, the improvement wherein the composition is rendered resistant to adverse effects of ascorbate by the presence in the composition of a complex of Co(III).

2. The composition of claim 1 wherein the indicator comprises benzidine, o-tolidine, 3,3',5,5'-tetra(lower alkyl)-benzidine, 2,7-diaminofluorene or mixtures thereof.

3. The composition of claim 2 wherein said complex is cobalt (III) hexamminetrichloride.

4. A test device for determining the presence of a peroxidatively active substance in a test sample comprising a carrier matrix incorporated with the composition of claim 3.

5. A method for determining the presence of a peroxidatively active substance in a test sample comprising the sequential steps of contacting the sample with the device of claim 4 and observing a detectable response therein.

6. A test device for determining the presence of a peroxidatively active substance in a test sample comprising a carrier matrix incorporated with the composition of claim 2.

7. A method for determining the presence of a peroxidatively active substance in a test sample comprising the sequential steps of contacting the sample with the device of claim 6 and observing a detectable response therein.

8. The composition of claim 1 wherein the organic hydroperoxide is cumene hydroperoxide and the indicator is 3,3',5,5'-tetra(lower alkyl)benzidine.

9. The composition of claim 8 wherein said complex is cobalt (III) hexamminetrichloride.

10. A test device for determining the presence of a peroxidatively active substance in a test sample comprising a carrier matrix incorporated with the composition of claim 9.

11. A method for determining the presence of a peroxidatively active substance in a test sample comprising the sequential steps of contacting the sample with the device of claim 10 and observing a detectable response therein.

12. A test device for determining the presence of a peroxidatively active substance in a test sample comprising a carrier matrix incorporated with the composition of claim 8.

13. A method for determining the presence of a peroxidatively active substance in a test sample comprising the sequential steps of contacting the sample with the device of claim 12 and observing a detectable response therein.

14. The composition of claim 1 wherein said complex is $Co(NH_3)_6Cl_3$.

15. A test device for determining the presence of a peroxidatively active substance in a test sample comprising a carrier matrix incorporated with the composition of claim 14.

16. A method for determining the presence of a peroxidatively active substance in a test sample comprising the sequential steps of contacting the sample with the device of claim 15 and observing a detectable response therein.

17. A test device for determining the presence of a peroxidatively active substance in a test sample comprising a carrier matrix incorporated with the composition of claim 1.

18. A method for determining the presence of a peroxidatively active substance in a test sample comprising the sequential steps of contacting the sample with the device of claim 17 and observing a detectable response therein.

19. A method for preparing a test device for determining the presence of a peroxidatively active substance in a test sample, wherein the device is resistant to the interfering effects of ascorbate present in the sample, said method comprising the sequential steps of preparing a first solution of a Co(III) complex in water, incorporating the first solution with a carrier matrix by wetting the matrix with the first solution, drying the wetted matrix to leave a residue of Co(III) complex, preparing a second solution of an organic hydroperoxide selected from the group consisting of t-butyl hydroperoxide, cumene hydroperoxide, diisopropylbenzene hydroperoxide, 2,5-dimethylhexane-2,5 dihydroperoxide, paramenthane hydroperoxide, or mixtures thereof, and an indicator in water or other suitable solvent the indicator being capable of providing a detectable response in the presence of the peroxide and the peroxidatively active substance, incorporating the second solution with the dried carrier matrix by wetting the matrix with the second solution, and drying the matrix to leave a combined residue of the Co(III) complex, the organic peroxide, and the indicator substance.

20. The method of claim 19 wherein the indicator comprises benzidine, o-tolidine, 3,3',5,5'-tetra(lower alkyl) benzidine, 2,7-diaminofluorene or mixtures thereof.

21. The method of claim 20 wherein the Co(III) complex is $Co(NH_3)_6Cl_3$.

22. The method of claim 19 wherein the Co(III) complex is $Co(NH_3)_6Cl_3$.

23. The method of claim 19 wherein the indicator is 3,3',5,5'-tetramethylbenzidine and the Co(III) complex is $Co(NH_3)_6Cl_3$.

* * * * *